(12) United States Patent
Passaglia

(10) Patent No.: US 9,314,375 B1
(45) Date of Patent: Apr. 19, 2016

(54) METHOD FOR AUTO-REGULATION OF INTRAOCULAR PRESSURE

(71) Applicant: Christopher Lawrence Passaglia, Lutz, FL (US)

(72) Inventor: Christopher Lawrence Passaglia, Lutz, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/680,395

(22) Filed: Apr. 7, 2015

Related U.S. Application Data

(62) Division of application No. 14/150,413, filed on Jan. 8, 2014, now Pat. No. 9,022,968.

(60) Provisional application No. 61/750,126, filed on Jan. 8, 2013.

(51) Int. Cl.
*A61F 9/007* (2006.01)
*A61M 5/142* (2006.01)
*A61M 5/145* (2006.01)

(52) U.S. Cl.
CPC ..... *A61F 9/00781* (2013.01); *A61F 2250/0013* (2013.01); *A61M 5/145* (2013.01); *A61M 5/1422* (2013.01); *A61M 5/14212* (2013.01); *A61M 5/14216* (2013.01); *A61M 2205/3341* (2013.01); *A61M 2205/3344* (2013.01)

(58) Field of Classification Search
CPC ............ A61F 9/00781; A61M 1/0031; A61M 1/0058; A61M 1/0068; A61M 2205/3344; A61M 2210/0612; A61M 2205/3341; A61M 5/142; A61M 5/14212; A61M 5/14216; A61M 5/1422; A61M 5/145; A61M 5/1452; A61M 5/48; A61M 5/482; A61M 5/484; A61M 5/486; A61M 5/488; A61M 2025/0001; A61M 2025/0002; A61M 2205/3331; A61M 5/007; A61B 17/12036; A61B 17/12099; A61B 17/12109; A61B 17/12136; A61B 17/22; A61B 2017/00292; A61B 2017/22082; A61B 2019/464

See application file for complete search history.

(56) References Cited

U.S. PATENT DOCUMENTS

| 4,909,783 | A | * | 3/1990 | Morrison | ............ | A61M 1/0058 604/121 |
|---|---|---|---|---|---|---|
| 5,830,176 | A | * | 11/1998 | Mackool | ............ | A61F 9/00745 604/22 |
| 2004/0111050 | A1 | * | 6/2004 | Smedley | ............ | A61M 27/002 604/9 |
| 2004/0167415 | A1 | * | 8/2004 | Gelfand | ............ | A61B 17/12036 600/500 |
| 2004/0176750 | A1 | * | 9/2004 | Nelson | ............ | A61M 5/14276 604/891.1 |

(Continued)

OTHER PUBLICATIONS

Quigley. Neuronal Death in Glaucoma. Prog Retin Eye Res. 1998. vol. 18 (No. 1): 39-57.

(Continued)

*Primary Examiner* — Adam Marcetich
(74) *Attorney, Agent, or Firm* — David Hendricks; Michele L. Lawson; Smith & Hopen, P.A.

(57) ABSTRACT

A method for controlling intraocular eye pressure via fluid exchange in the body is presented. The method may comprise providing a system to sense and regulate pressure, then implanting the system into the eye. The system may comprise four main components: a cannula, a sensor, a controller and a pump. The method works to engage in a fluid exchange which slowly increases/decreases intraocular pressure until a desired level is reached. Once the desired level is reached, the intraocular pressure is held steady and any external pressure perturbations are removed.

5 Claims, 10 Drawing Sheets

(56) References Cited

U.S. PATENT DOCUMENTS

| | | | | |
|---|---|---|---|---|
| 2006/0052666 | A1* | 3/2006 | Kumar | A61M 1/0058 600/159 |
| 2008/0146993 | A1* | 6/2008 | Krishna | A61M 5/142 604/65 |
| 2009/0163853 | A1* | 6/2009 | Cull | A61M 1/0031 604/35 |
| 2010/0063483 | A1* | 3/2010 | Adahan | A61M 1/0088 604/543 |
| 2011/0015512 | A1* | 1/2011 | Pan | A61B 3/16 600/399 |
| 2011/0054385 | A1* | 3/2011 | Eichler | A61M 1/0058 604/22 |
| 2011/0201874 | A1* | 8/2011 | Birk | A61F 5/003 600/37 |
| 2014/0039374 | A1* | 2/2014 | Dos Santos | A61B 3/16 604/9 |

OTHER PUBLICATIONS

Morrison et al., Understanding mechanisms of pressure-induced optic nerve damage. Prog Retin Eye Res. 2005. vol. 24: 217-40.
Salt and Plontke. Endolymphatic hydrops pathophysiology and experimental models. Otolaryngol Clin North Am. 2010. vol. 43: 971-83.
Wells and Crampton. A portable bio-amplifier for electric fish research: design and construction. Neotrop Ichthyol. 2006. vol. 4 (No. 2):295-9.
John. Mechanistic insights into glaucoma provided by experimental genetics. The Cogan Lecture. Invest Ophthalmol Vis Sci. 2005. vol. 46 (No. 8): 2650-2661.
McKinnon et al., Mouse models of retinal ganglion cell death and glaucoma. Exp Eye Res. 2009. vol. 88: 816-24.
Almasieh et al., The molecular basis of retinal ganglion cell death in glaucoma. Prog Retin Eye Res 2012. vol. 31: 152-81.
Gaasterland and Kupfer. Reports: Experimental glaucoma in rhesus monkey. Invest Ophthalmol Vis Sci. 1974. vol. 13 (No. 6): 455-57.
Quigley and Hohman. Reports: Laser energy levels for trabecular meshwork damage in the primate eye. Invest Ophthalmol Vis Sci. 1983. vol. 24:1305-7.
Aihara et al., Experimental mouse ocular hypertension: establishment of the model. Invest Ophthalmol Vis Sci. 2003. vol. 44 (No. 10): 4314-20.
Mateijsen et al., Perilymphatic pressure measurement in patients with Meniere's disease. Eur Arch Otorhinolaryngol. 2001. vol. 258: 1-4.
Garcia-Valenzuela et al., Programmed cell death of retinal ganglion cells during experimental glaucoma. Exp Eye Res. 1995. vol. 61: 33-44.
Grozdanic et al., Temporary elevation of the intraocular pressure by cauterization of vortex and episcleral veins in rats causes functional deficits in the retina and optic nerve. Exp Eye Res. 2003. vol. 77:27-33.
Morrison et al., A rat model of chronic pressure-induced optic nerve damage. Exp Eye Res. 1997. vol. 64:85-96.
Gross et al., A mouse model of elevated intraocular pressure: retina and optic nerve findings. Trans Am Ophthalmol Soc. 2003. vol. 101:163-9.
Ruiz-Ederra et al., The pig eye as a novel model of glaucoma. Exp Eye Res. 2005. vol. 81: 561-9.
Ruiz-Ederra and Verkman. Mouse model of sustained elevation in intraocular pressure produced by episcleral vein occlusion. Exp Eye Res. 2006. vol. 82:879-84.
Fu and Sretavan. Laser-induced ocular hypertension in albino CD-1 mice. Invest Ophthalmol Vis Sci. 2010. vol. 51 (No. 2): 980-90.
Sappington et al, The microbead occlusion model: a paradigm for induced ocular hypertension in rats and mice. Invest Ophthalmol Vis Sci. 2010. vol. 51 (No. 1): 207-16.
Morrison et al., Pathophysiology of human glaucomatous optic nerv damage: insights from rodent models of glaucoma. 2011. Exp Eye Res. vol. 93:156-64.

Katz and Robinson. Evidence of cell loss from the rat retina during senescence. Exp Eye Res. 1986. vol. 42: 293-304.
Selles-Navarro et al., Retinal ganglion cell death after different transient periods of pressure-induced ischemia and survival intervals: a quantitative in vivo study. Invest Ophthalmol Vis Sci. 1996. vol. 37 (No. 10): 2002-14.
Cepurna et al., Age related optic nerve axonal loss in adult Brown Norway rats. Exp Eye Res. 2005. vol. 80:877-84.
Passaglia et al., Orientation sensitivity of ganglion cells in primate retina. Vision Res. 2002. vol. 42: 683-694.
Freeman et al., Single-unit in vivo recordings from the optic chiasm of rat. J Vis Exp. 2010. vol. 38, pii: 1887.
Heine and Passaglia. Spatial receptive field properties of rat retinal ganglion cells. Vis Neurosci. 2011. vol. 28 :403-17.
Schnell et al., Measurement of intraocular pressure by telemetry in conscious unrestrained rabbits. Invest Ophthalmol Vis Sci. 1996. vol. 37 (No. 6): 958-965.
McLaren et al. Continuous measurement of intraocular pressure in rabbits by telemetry. Invest Ophthalmol Vis Sci. 1996. vol. 37 (No. 6): 966-75.
Passaglia et al., Tono-Pen XL calibration curves for cat, cow, and sheep. Vet Ophthalmol. 2004. vol. 7 (No. 4): 261-4.
Li and Liu. Telemetric monitoring of 24h intraocular pressure in conscious freely moving C57BL/6J and CBA/Caj mice. Mol Vis. 2008. vol. 14:745-9.
Xue et al., A Su-8-based compact implantable wireless pressure sensor for intraocular pressure sensing application. 33rd Annual International Conf Proc IEEE Eng Med Biol Soc. 2011: 2854-7.
Todani et al., Intraocular pressure measurement by radio wave telemetry. Invest Ophthalmol Vis Sci. 2011. vol. 52 (No. 13): 9573-9580.
Ha et al., Polymer-based miniature flexible capacitive pressure sensor for intraocular pressure (IOP) monitoring inside a mouse eye. Biomed Microdevices. 2012. vol. 14: 207-15.
Leonardi et al. First steps toward non-invasive intraocular pressure monitoring with a sensing contact lens. Invest Ophthalmol Vis Sci. 2004. vol. 45 (No. 9): 3113-17.
Sánchez et al., Prototype of a nanostructured sensing contact lens for noninvasive intraocular pressure monitoring. Invest Ophthalmol Vis Sci. 2011. vol. 52 (No. 11): 8310-5.
El-Khatib et al., Adaptive closed-loop control provides blood-glucose regulation using dual subcutaneous insulin and glucagon infusion in diabetic Swine. J Diabetes Sci Technol. 2007. vol. 1 (Issue 2): 181-92.
Bruttomesso et al., Closed-loop artificial pancreas using subcutaneous glucose sensing and insulin delivery and a model predictive control algorithm: preliminary studies in Padova and Montpellier. J Diabetes Sci Technol. 2009. vol. 3 (Issue 5): 1014-21.
Jacobs et al., Development of a fully automated closed loop artificial pancreas control system with dual pump delivery of insulin and glucagon. Conf Proc IEEE Eng Med Biol Soc. 2011: 397-400.
Freeman et al., The maintained discharge of rat retinal ganglion cells. Vis Neurosci. 2008. vol. 25:535-548.
Heine and Passaglia. Spatial receptive field properties of rat retinal ganglion cells. Vis Neurosci. 2011. vol. 28:403-17.
Sun et al., Enhanced peripheral chemoreflex function in conscious rabbits with pacing-induced heart failure. J Appl Physiol. 1999. vol. 86 (No. 4): 1264-1272.
Molteno. New implant for drainage in glaucoma: clinical trial. Brit J Ophthalmol. 1969. vol. 53: 606-615.
Hughes. A schematic eye for the rat. Vision Res. 1979. vol. 19: 569-88.
Akula et al., The anatomy of the rat eye with oxygen-induced retinopathy. Doc Ophthalmol. 2010. vol. 120: 41-50.
Shiose et al., Epidemiology of glaucoma in Japan—a nationwide glaucoma survey. Jpn J Ophthalmol. 1991. vol. 35:133-55.
Klein et al., Prevalence of glaucoma. The Beaver Dam Eye Study. Ophthalmology 1999: 1499-1504.
Raviv et al., Pericardial patch grafts in glaucoma implant surgery. J Glaucoma. 1998. vol. 7: 27-32.
Ueda et al., Experimental glaucoma model in the rat induced by laser trabecular photocoagulation after an intracameral injection of India ink. Jpn J Ophthalmol. 1998. vol. 42: 337-44.

(56) References Cited

OTHER PUBLICATIONS

Morrison et al., A rat model of pressure-induced optic nerve damage. Exp. Eye Res. 1997. vol. 64: 85-93.
Cavallotti et al., Age-related changes in rat retina. Jpn J Ophthalmol. 2001. vol. 45:68-75.
Walter et al., Development of a completely encapsulated intraocular pressure sensor. Ophthalmic Res. 2000. vol. 32: 278-84.
Ball et al., Brown's superior oblique tendon syndrome after Baerveldt glaucoma implant. Arch Ophthalmol. 1992. vol. 110: 1368.

* cited by examiner

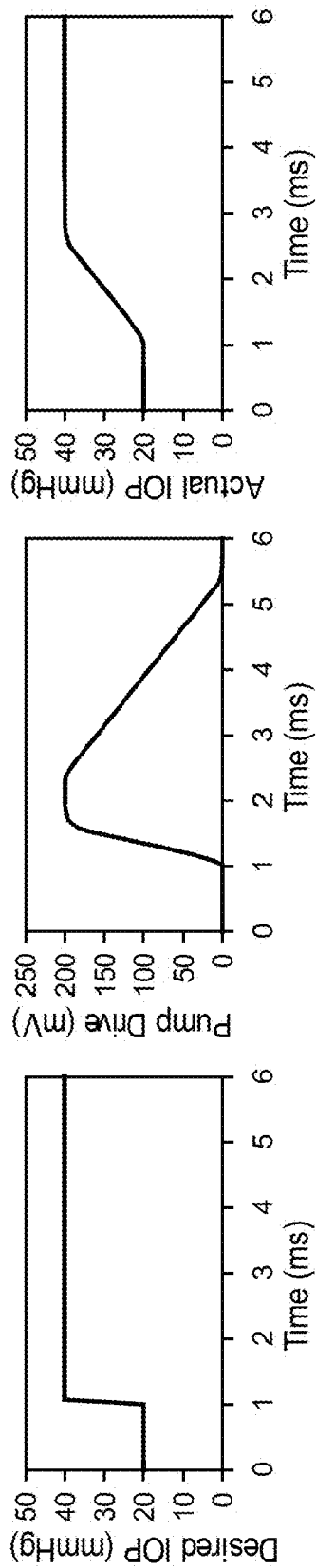

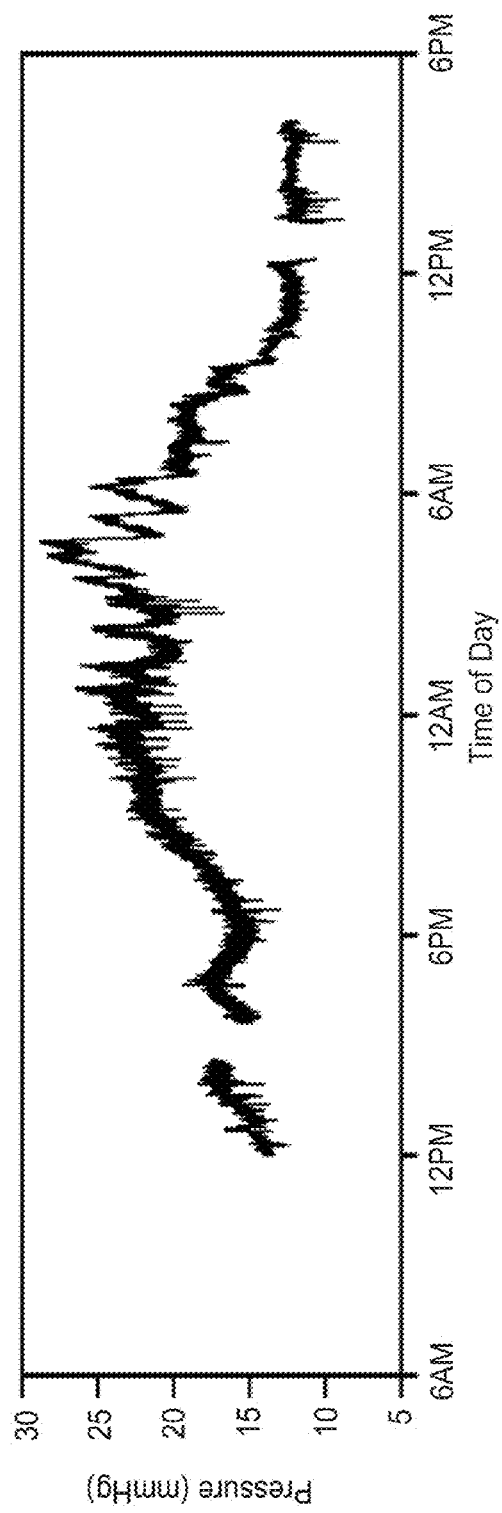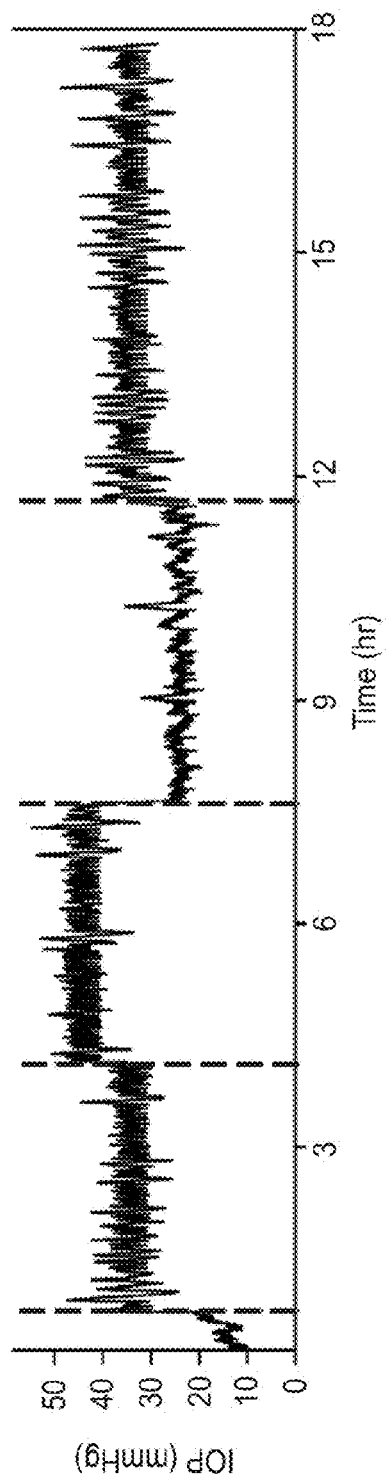
FIG. 7A
FIG. 7B

METHOD FOR AUTO-REGULATION OF INTRAOCULAR PRESSURE

CROSS-REFERENCE TO RELATED APPLICATIONS

This application is a divisional of and claims priority to currently pending U.S. patent application Ser. No. 14/150,413, entitled "AUTO-REGULATION SYSTEM FOR INTRAOCULAR PRESSURE", filed Jan. 8, 2014, which claims priority to provisional U.S. Patent Application Ser. No. 61/750,126, filed on Jan. 8, 2013, titled "AUTO-REGULATION SYSTEM FOR INTRAOCULAR PRESSURE," which is hereby incorporated by reference in its entirety.

FIELD OF INVENTION

This invention relates to devices for use with human or animal bodies. Specifically, the invention provides a pressure regulated miniature pump to automatically control the intraocular pressure of the eye.

BACKGROUND OF THE INVENTION

Glaucoma is a collection of ocular disorders that preferentially targets retinal ganglion cells for injury and eventually causes blindness if left untreated. A common feature of the disease is an increase in IOP caused by a reduction in outflow of aqueous fluid through the trabecular meshwork of the eye. The pressure increase can happen rapidly in the case of angle-closure glaucoma due to the iris coming in sudden contact with the meshwork, or it can proceed slowly in the case of open-angle glaucoma due a gradual decline in the outflow capacity of the eye.

The open-angle form is most prevalent and insidious because the symptoms are subtle and easily overlooked. By the time a clinical diagnosis is typically made, around half the population of retinal ganglion cells has already died [1]. This is tragic since the progression of the disease can be slowed with medicines that lower IOP. Part of the reason for the late diagnosis is not just the lack of awareness of a problem but also that ocular hypertension is not an obligatory feature of the disease. Some people with high IOP never show any signs of retinal injury, while others with normal IOP have pronounced visual deficits [3, 4]. Additional evidence is therefore needed from gonioscopy exams, optic disc inspections, and vision tests before the risks and costs of surgical or pharmacological intervention are acceptable and treatment is initiated.

Since retinal ganglion cells are irreplaceable at present time, there is a great need for a detailed understanding of what happens to the cells before they die so that the onset of the disease can be detected and treatment commenced at the earliest possible date. Such an understanding is difficult to obtain clinically because the structural and functional state of individual ganglion cells can only be accessed using invasive techniques. Researchers thereby rely heavily on animal models in which IOP is chronically increased by genetic or experimental means in order to learn about the mechanisms by which glaucoma inflicts damage upon the retina.

Genetic models of glaucoma are presently restricted to select strains of mice, the most studied of which is the DBA/2J inbred line. These mice have a mutation which causes iris pigment to slough off and accumulate in the trabeculum at around 6-8 months of age [5]. Since the ciliary body continues to produce aqueous fluid, the ensuing buildup of pressure in the eye leads to impaired retrograde transport, retrograde axonal degeneration, and then ganglion cell body apoptosis much like in humans [5, 6]. Genetic models have the advantages that the IOP increase is spontaneous, gradual like open-angle glaucoma, and automatic for every animal, which makes it possible to apply modern molecular tools to identify the critical genes and biochemical pathways involved in ganglion cell death [6, 7].

Disadvantages are that i) the mutations behind the model (since animals do not normally get glaucoma) has multiple cellular effects not all of which are known or ascribable to pressure, ii) the mutational effects are generally bilateral so there is no internal control group for statistical comparisons, iii) the time of onset is uncertain without frequent IOP measurement, and iv) the small size of mice can be inconvenient for pressure monitoring and physiological testing.

Experimental models of glaucoma include a diversity of species and induction techniques. The first model to achieve widespread success was created in primate [8, 9], and later replicated in other mammals [10, 11], by photocoagulating the trabecular meshwork with an intense laser. Subsequently, rat models were introduced which target outflow pathways downstream of the meshwork for occlusion [12, 13]. One method is to cauterize episcleral veins on the eye surface, but the method has lost favor because the IOP elevation often dissipates after a few weeks [14] and the pattern of retinal damage differs noticeably from that in humans [2]. The more popular and established method is to inject a bolus of hypertonic saline into an episcleral vein [12, 15].

The saline scleroses limbal vasculature of the eye, causing IOP to rise over a couple weeks to a roughly sustained level that can last for months. These methods and variants of them have since been applied to mice and pigs [6, 16-19], and others are currently being explored such as intraocular injection of latex microspheres [20]. What is striking and exciting about these experimental models is that an injury inflicted solely to the front of the eye causes at the back of the eye an accumulation of organelles in the optic nerve head, a removal of optic disc capillaries and deposition of extracellular matrix proteins, and a preferential loss of large ganglion cells with non-ganglion cells left relatively untouched [1, 2, 21].

Experimental models have several advantages over genetic models for glaucoma research and some notable disadvantages. The main advantage is that only one eye experiences high IOP so the other eye can serve as a built-in control for hypothesis testing, which is especially important when the pressure exposure history is long because rodent eyes can undergo measurable age-related loss of ganglion cell number and function [22-24]. A second advantage is that the animal is physiologically normal in all respects except the treated eye. Optic nerve damage can therefore be causally linked to the treatment and in all likelihood to elevated IOP since it is the lone feature shared by the various experimental treatments. A third advantage is that ganglion cell activity can be recorded in rats and primates, but not as yet in mice, without disturbing or removing the eye or brain [25-27]. This allows for chronological studies of the changes in optic nerve information sent to the brain as the disease progresses. The main disadvantage is that IOP increases are not spontaneous so certain questions are impractical to address by experimental models in lieu of costs in time and effort.

While current methods of glaucoma induction in animal models are effective and widely employed, their usefulness for glaucoma research has important limitations [21]. For one, multiple experimental treatments are often necessary to suppress fluid outflow and raise IOP to a detrimental level, and even then some animals still do not develop ocular hypertension or the pressure increase is short-lasting. Multiple injections may result in as much as a month of time wasted checking whether the first injection was successful. Secondly, IOP must be frequently monitored to evaluate treatment success and chronicle the exposure history. This is impractical to do by hand with a tonometer, meaning that momentary variations in pressure over the course of a day go unrecorded. And thirdly, the temporal progression and amount of IOP change a given animal will experience is largely unpredictable.

Loosely similar pressure profiles can be expected, but the steady-state level might be higher or lower, might be reached more or less quickly, and might not go through peaks or midlevel plateaus. Such differences in pressure exposure could have an important bearing on disease pathology. A systematic, carefully controlled study of the effects of pressure history is currently impossible.

These limitations present a major impediment to continued progress in glaucoma research. As engineers know, in order to fully and correctly identify the properties of an unknown system from its outputs, the corresponding inputs to the system must be precisely specified and broadly distributed in strength and time. Yet, the state-of-the-art at the moment is to inject an agent into the eye and take occasional IOP readings in hopes that something happens.

Given these challenges, what is needed is a device and system that is capable of giving clinicians complete control of eye pressure as well as round-the-clock feedback on pressure for managing that control.

SUMMARY OF INVENTION

Various embodiments of the present invention include systems and methods for regulating pressure within a portion of a human or animal body. An exemplary system may comprise a bidirectional pump, a cannula, a pressure sensor, and a controller. The pump may comprise a motor, a fluid drive unit coupled to the motor, and a reservoir containing fluid. A pressure sensor may be coupled to the reservoir. The controller may be operatively coupled to the pump and pressure sensor.

An exemplary method for regulating intraocular eye pressure may comprise providing a bidirectional pump, a cannula, a pressure sensor, and a controller. The pump, cannula, pressure sensor and controller may be implanted in the eye. At least a portion of the cannula may be inserted into an anterior chamber of the eye. Fluid pressure within the anterior chamber may be senseded, and a signal sent to the controller. The controller may receive the signal and compare the signal to a set point. The pump may operate in a first direction when the signal is below the set point, or the pump may operate in a second direction when the signal is above the set point.

BRIEF DESCRIPTION OF THE DRAWINGS

For a fuller understanding of the invention, reference should be made to the following detailed description, taken in connection with the accompanying drawings, in which:

FIG. 6A is a graph of a simulated input to the circuit illustrated in FIG. 5. The input signal is a step change in a set point of the circuit.

FIG. 6B is a graph of a simulated voltage signal sent by the circuit illustrated in FIG. 5 to a pump motor in response to the set point change shown in FIG. 6A.

FIG. 6C is a graph of a simulated pressure response of the circuit illustrated in FIG. 5 to a pump driven according to the voltage illustrated in FIG. 6B.

FIG. 7A is a graph of intraocular pressure measured using the system of FIG. 1.

FIGS. 7B and 7C are graphs intraocular pressure measured and regulated using the system of FIG. 1, which held pressure at 25, 35, and 45 mmHg for various lengths of time.

DETAILED DESCRIPTION OF THE PREFERRED EMBODIMENT

Figure 1:
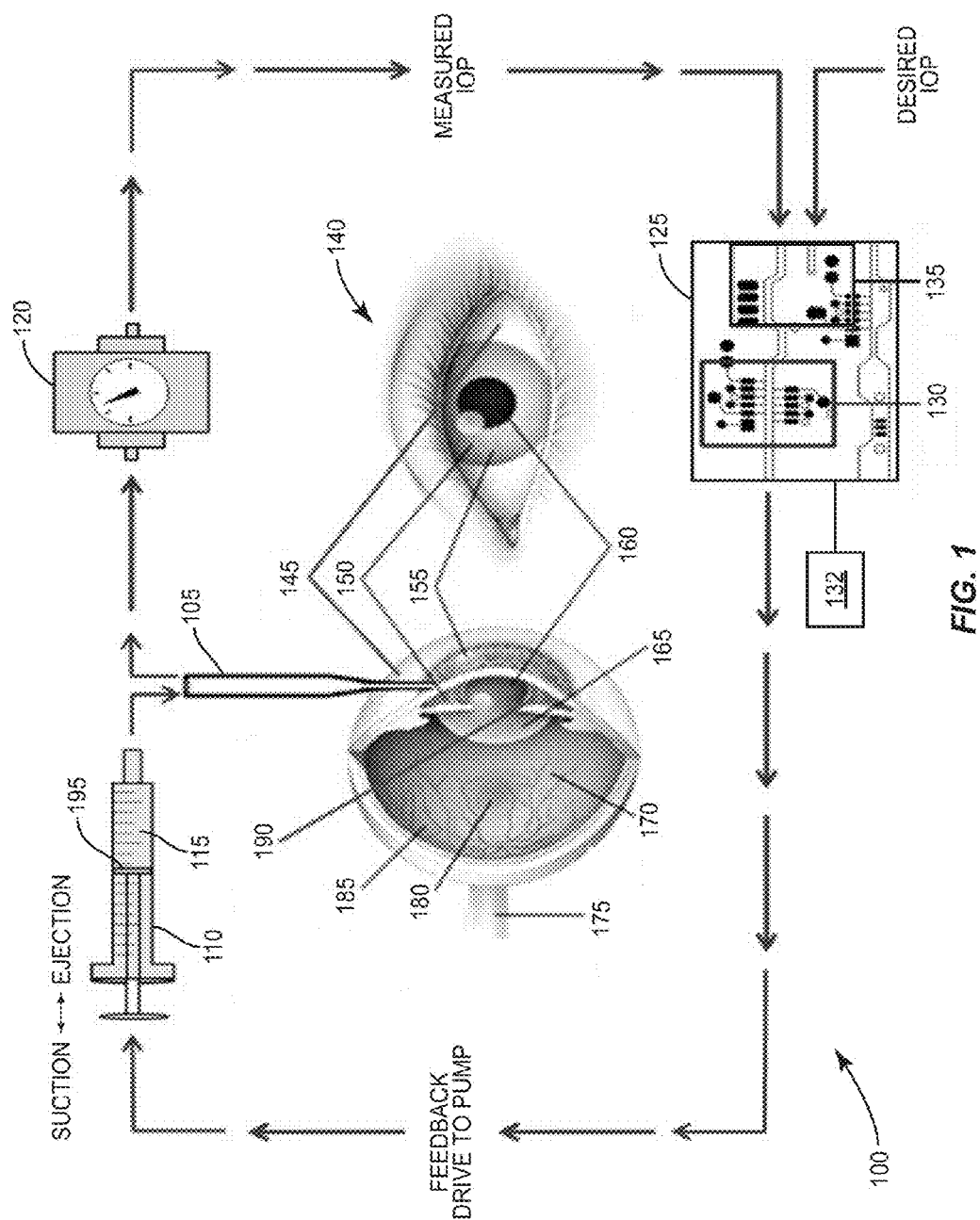
FIG. 1 is a schematic view of a system for regulating intraocular eye pressure.

In the following detailed description of the preferred embodiments, reference is made to the accompanying drawings, which form a part hereof, and within which are shown by way of illustration specific embodiments by which the invention may be practiced. It is to be understood that there may be other embodiments by which the invention may be practiced. It is to be understood that other embodiments may be utilized and structural changes may be made without departing from the scope of the invention.

The invention disclosed herein is a pressure-regulated miniature pump that automatically controls the IOP of the eye in humans and animals. The invention is intended for use in clinical treatment and/or animal research of glaucoma, an ocular disease associated with chronically elevated IOP levels. The invention also has broad application as an implantable pump within or on any part of a human or animal body for programmable delivery of small volumes of fluid or drugs. The invention also has broad application as a pressure monitoring and/or recording device for areas within a human or animal body.

Various embodiments of the invention may comprise an implantable and programmable device for delivering or extracting very small volumes of fluid to or from the body. The device has multiple possible applications, and one in particular is the automatic regulation and monitoring of the intraocular pressure of the eye. This application would have commercial value for glaucoma induction in research animals and for glaucoma treatment in human patients. The device will for the first time enable researchers to manipulate pressure in whatever manner desired, giving them complete and reproducible control of the specific input parameters they want to investigate experimentally.

The device and system to autonomously regulate IOP via a pressure sensitive microfluidic pumping system is presented herein and consists of four main elements: 1) a fine cannula positioned in the anterior chamber of the eye, 2) a pressure sensor coupled to the cannula, 3) a controller circuit, and 4) a bidirectional pump.

The pressure sensor transduces IOP via the catheter into an electronic signal which the controller circuit compares against a reference signal that represents the desired IOP level. The controller uses the difference signal to drive the pump motor. Forward piston motion raises IOP by ejecting fluid into the eye, and backward motion lowers IOP by aspirating fluid into the catheter. Once the set point is reached, IOP is effectively locked there as other pressure influences are removed by the system. The set point can lie above or below the resting IOP of the eye, and the system can be configured to move IOP to the set point at a prescribed rate or vary IOP in time with any desired waveform. A wide variety of pressure history profiles can thus be methodically investigated with repeatable precision in basically every animal. The smart pump also has applications for treating the disease clinically and for investigating other pressure-related neurological conditions.

FIG. 1 provides a schematic of various embodiments of a system 100 adapted to actively regulate IOP with a pressure-sensitive microfluidic pump. In various embodiments, the system 100 may regulate pressure within a portion of a human or animal body, such as a mammalian eye 140 illustrated in FIG. 1. The eye 140 may comprise cornea 155 surrounded by a sclera, which together generally form an outer surface of the eye 140. A pupil 160 connected to an iris 150 is position behind the cornea 155, forming an anterior chamber 190 therebetween. The interior portion of the eye 140 is filled with vitreous humor 170. An inner surface of the eye is lined with the retina 185 comprised of a thin layer of tissue. A macula 180 is positioned within the retina, and an optic nerve 175 is coupled to the retina 185 at the back of the eye 140.

As illustrated in FIG. 1, the system 100 may comprise a fine catheter tube 105 filled with artificial aqueous humor 115, inserted in the anterior chamber 190 of the eye 140, and sutured in place to the sclera 145. The fluid-filled catheter 105 conducts IOP directly to a pressure sensor 120, which transduces IOP to a voltage signal. A controller 125 comprising a comparator circuit 135 and a regulator circuit 130 (and a power source, not shown) compares the measured pressure signal with a reference signal (set point) corresponding in voltage to the desired IOP level. Based on the difference between measured and desired pressure voltages, the regulator circuit 130 of the controller 125 sends a drive signal to a dc motor (see FIG. 3) inside the pump 110. A positive drive causes the pump piston 195 to move forward, ejecting aqueous fluid 115 out the catheter 105, while a negative drive causes the pump piston 195 to move backward, drawing fluid into the catheter 105 from the anterior chamber 190. The fluid exchange leads to a slow increase/decrease in IOP, which continues until the desired pressure level is reached. The system 100 then holds IOP steady at the desired level as the sensor-controller-pump feedback loop removes any external pressure perturbations. The system 100 may also comprise a wireless transmitter circuit 132 to report measured IOP either intermittently or continuously to the user. In short, the system 100 acts like a pressure clamp for glaucoma induction in animals or glaucoma management in humans. Moreover, the system 100 can be configured to lower IOP as well as raise it, and thus is clinically useful for the treatment of glaucoma and other pressure-based neurodegenerative conditions. In broader terms, the system 100 may function as a pressure clamp for neurological research like a voltage clamp amplifier is for cellular physiology research.

In various embodiments, the pressure sensor 120 could be replaced with an alternate sensor to measure a parameter other than pressure and produce a voltage signal to be sent to the controller 125. For example, the sensor could sense pH, temperature, conductivity, concentration of a compound (such as a medicant, an ion, a hormone, a protein, and the like), or any other parameter known in the art. In these embodiments, the pump 110 may deliver a medicant or other treatment in response to the sensed parameter.

Although the virtues of closed-loop feedback are familiar to engineers, a comparable system does not exist commercially or non-commercially for controlling extremely small volumes of fluid in a medical application. A telemetric pressure sensor, which uses a fluid-filled catheter inserted into the eye to conduct IOP to a head-mounted transducer [28, 29, 31], is available. However, such systems do not include the closed-loop feedback system of the current invention to not only monitor but to also vary the IOP. With the advance of microfabrication techniques the catheter approach is being supplanted by wireless sensors implanted in the eye, some of which are near to market launch (Implandata Ophthalmic Products GmbH, Hanover, Germany). Implantable sensors generally consist of a capacitive-transducer circuit encased in biocompatible material with a small antenna for electromagnetic powering and pressure readout via an external instrument [30, 32-34]. The catheter and implantable sensors both measure IOP directly like the proposed system (unlike a tonometer or contact-lens transducer [35, 36]), but they differ from it in two key respects: they lack a fluid pump and a feedback controller. The cannula 100 may be similar to tube shunts used for glaucoma treatment, such as the Ahmed shunt. Various pressure-sensitive valves have been designed or proposed for these shunts to relieve pressure buildup. The system 100 may differ from such shunts as the system 100 may comprise a pump 110 and a controller 125 for raising pressure or varying pressure in time in any desired manner, as well as a pressure sensor for continuously reporting IOP to the user.

The system 100 may comprise four components: cannula 105, sensor 120, controller 125, and bidirectional pump 110. The detailed design of each component is dependent on the planned usage of the system 100. For example, the size of the pump 110 would scale with the volume of fluid 115 it must accommodate, which is turn could influence the drive signal that the controller 125 outputs, and so forth. A prototype system 100 was developed for inducing glaucoma in rats in order to study the disease; however, this use is exemplary and the invention is not limited to use with glaucoma. The four main components of the system 100 are described below.

Ocular Cannula

The ocular cannula 105 (or catheter tube) may be a short length of fine flexible tubing, which can be purchased commercially (e.g., MicroRenathane®, Braintree Scientific, Braintree, Mass.). This tubing material can conduct arterial pressure for days without clogging [42].

Before translimbal insertion into the eye 140, the cannula 105 may be filled with artificial aqueous humor 115 (NaCl: 113 mM, KCl: 4.5 mM, $MgCl_2$: 1 mM, $CaCl_2$: 1.5 mM, glucose: 6 mM, $NaHCO_3$: 20 mM, HEPES: 10 mM, and pH: 7.3 [43]), and tunneled subcutaneously from an incision in the spine or scalp to an opening in the conjunctiva (a thin coating on the sclera 145) made at the limbus, which is the border of the sclera 145 and the cornea 155 (the transparent part of the eye 140 covering the iris 150 and the pupil 160). The cannula 105 may be bevel cut and/or pre-shaped by heating to facilitate eye penetration and permanent attachment to the sclera 145. A needle of about the same diameter as the cannula 105 is then inserted into the anterior chamber 190, and through the needle hole the tip of the cannula 105 is inserted about 2 mm at an angle that avoids damaging the iris. The cannula 105 may be sutured to the sclera 145 and secured with tissue glue (Vetbond, 3M Comp., St Paul, Minn.). If necessary, the cannula 105 can be covered with grafts of donor tissue to prevent erosion of the conjunctiva and ocular infection. The cannula 105 design and placement is like that of Baerveldt (valveless) drainage tubes long used in human glaucoma patients [44, 45].

Figure 2A:
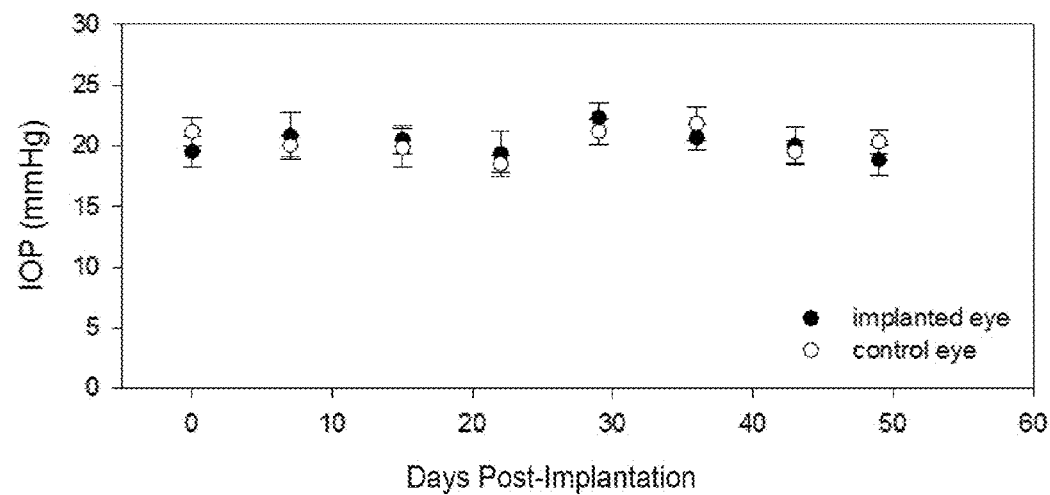
FIGS. 2A and 2B are graphs of intraocular eye pressure for two rats showing the pressure over a period of time for one eye with a cannula implanted and a second eye without a cannula as a control.
Figure 2B:
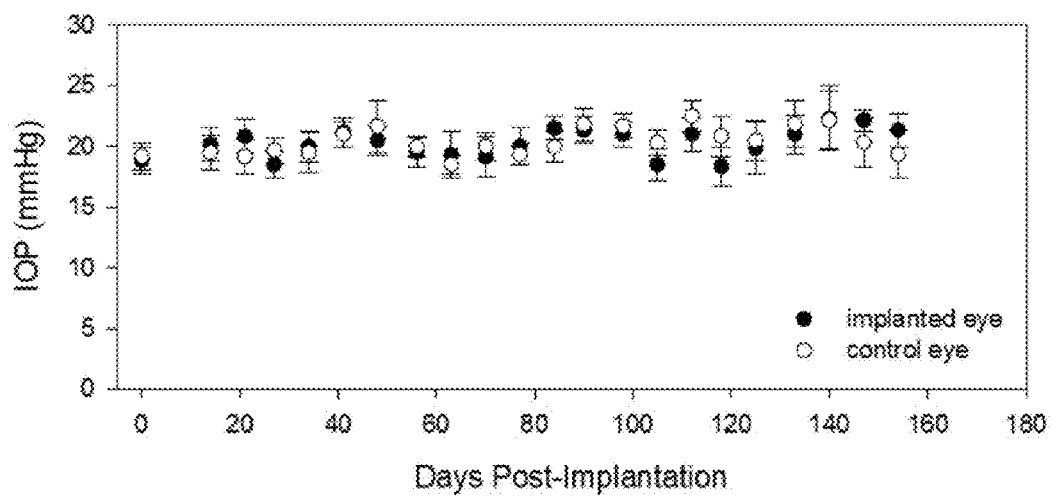

FIGS. 2A and 2B present the IOP history of two rat eyes 140 after implantation of the cannula 105. At least once per week, the animal was sedated with isoflurane and mean IOP was measured with a tonometer. Each point on the two graphs is the average of 6 tonometer readings, and the error bars provide the standard deviation of the readings. The control eye 140 was the other eye 140 (without a cannula 105 inserted) of the same animal. The IOP measurements of FIGS. 2A and 2B for the implanted eye 140 were unchanged from the non-implanted eye 140 after over 100 days of implantation, indicating that the cannula 105 does not cause fluid leakage. Rats have been implanted for several months with a cannula 105 with little or no sign of ocular inflammation or damage to internal structures even though the eye 140 blinks and freely moves.

Pressure Sensor

Figure 3:
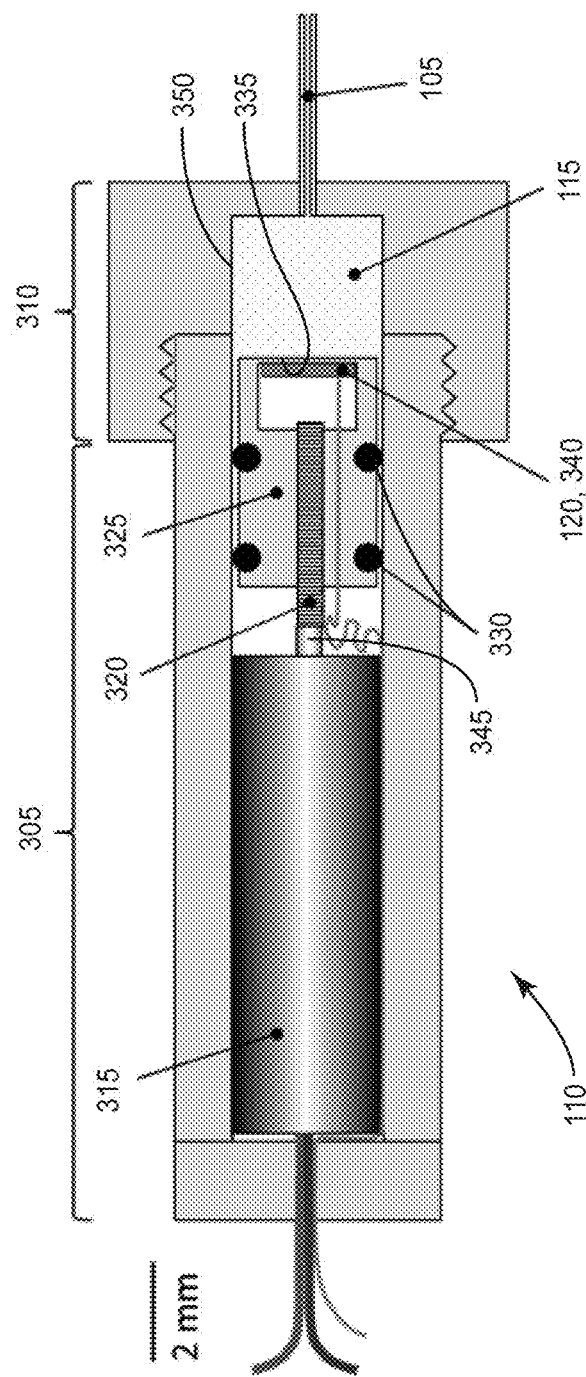
FIG. 3 is a cutaway view of a pump and pressure sensor

FIG. 3 illustrates various embodiments of the pump 110 and pressure sensor 120. The pressure sensor 120 may comprise a miniature strain gauge 340 mounted on an inside surface 335 of the pump piston 325, which may be hollow. Other locations for the pressure sensor 120 are possible, but locating the pressure sensor 120 within the piston 325 helps to keep size down as the system 100 aims to be implantable on rats and ultimately humans. For systems 100 using pumps 110 other than a syringe pump 110, the pressure sensor 120 may be in communication with a fluid reservoir 350. For uniform pressure, the strain distribution (E) is maximal at the center of the piston surface 335 and can be quantified by thin plate theory as $\epsilon = 3Pr(1-v^2)/8E\delta^2$, where P is pressure, r is diaphragm radius, $\delta$ is diaphragm thickness, $v$ is Poisson's ratio, and E is elastic modulus. The radius is constrained by the pump motor 315 and Poisson's ratio and elastic modulus specified by the pump material. The operating pressure is allowed to reach 100 mmHg to permit detection of ischemic IOP spikes. This leaves piston 325 thickness as a free parameter, which is determined along with strain gauge 340 sensitivity to generate a measureable voltage signal for the controller 125 to regulate. The system 100 may transmit the voltage signal wirelessly to a receiver as described further below for external logging of pressure data.

Figure 4A:
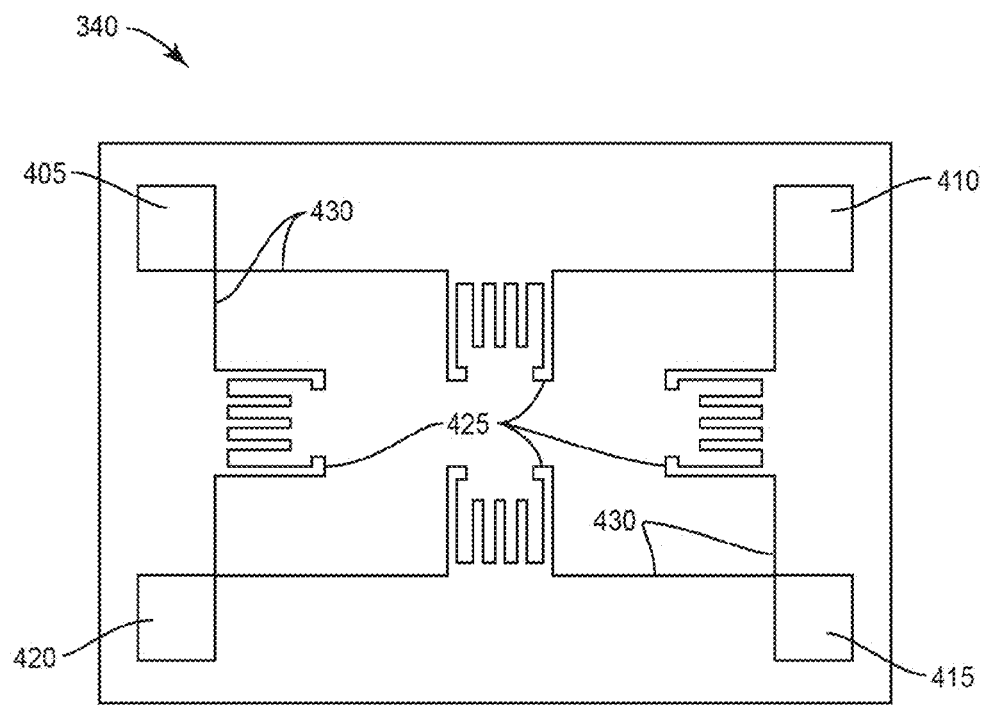
FIGS. 4A and 4B are schematic diagrams of a pressure sensor and diaphragm showing a top view and side view, respectively.
Figure 4B:
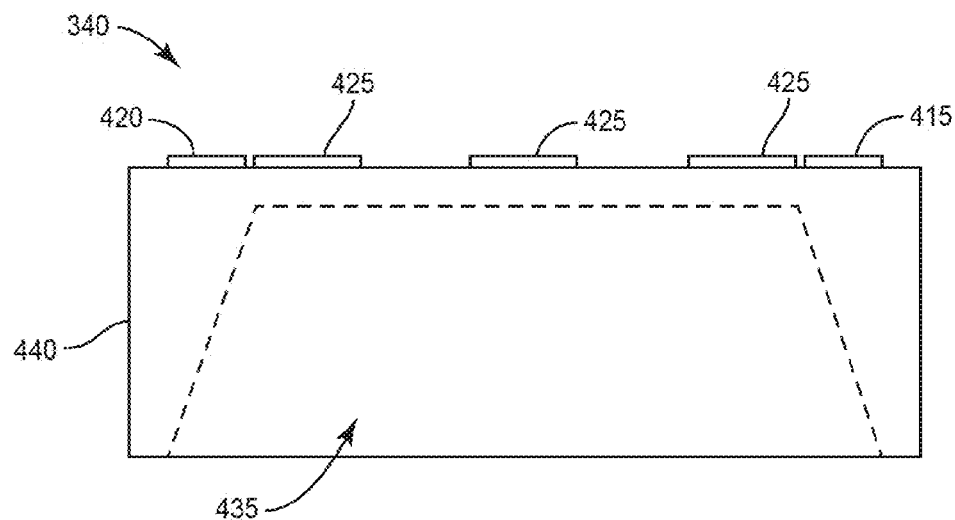

FIG. 4A illustrates a top schematic view and FIG. 4B illustrates a side schematic view of various embodiments of the strain gauge 340 of the pressure sensor 120. The strain gauge 340 may comprise piezoelectric resistors 425 coupled in a Wheatstone bridge configuration. Contact pads 420, 410 provide positive and negative power connections, and contact pad 415 provides a ground for the electrical circuit. A voltage signal may be taken from contact pad 405 corresponding to the strain sensed by the strain gauge 340. The strain gauge 340 may be coupled to a silicon diaphragm 440. The diaphragm 440 may comprise a hollow space 435 under the piezoelectric resistors 425 that is deformable in response to pressure exerted on the piston 325 by the fluid 115. As the diaphragm 440 deforms, the resistance of the piezoelectric resistors 425 varies, changing the output voltage at contact pad 405. The output voltage may be read by the circuitry of the controller 125. In various embodiments, the strain gauge 340 may have an operating range of about 0-60 mmHg, although one skilled in the art will readily recognize that larger or smaller ranges are within the scope of the present invention.

Fluid Pump

Returning to FIG. 3, the fluid pump 110 may comprise a plastic head piece 310 that connects to a plastic base piece 305 housing a dc motor 315, fine-threaded screw 320 coupled to a motor shaft 345, and a hollow piston 325 coupled to the screw 320. The pump head 310 is sized to accommodate the desired fluid 115 volume within a reservoir 350. In various embodiments, the pump volume may be approximately 10 µL, which is about the typical fluid volume of a rat eye 140 [47, 48]. The thread pitch of the screw 320 may be such that one full rotation of the motor shaft 345 causes influx/efflux of about 1 µL of fluid 115 through the catheter 105, which connects to the pump head piece 310. A base plate (not shown) may be used to attach the pump to the skull. O-rings 330 may provide a seal such that the fluid 115 in the reservoir 350 does not flow past the piston 325.

The operation of the pump 110 may resemble a syringe pump in that the motor 315 rotates the screw 320 which advances or retracts the piston 325 inside the enclosed fluid-filled reservoir or chamber 350 with the catheter 105 as an output port. In various embodiments, the fluid-filled chamber 350 (e.g., syringe) and pump motor 315 are not separate elements but one small implantable device. Other fluid drive units are possible as well, such as a peristaltic pump design where the motor rhythmically compresses the catheter to move fluid forward or backward. This design would allow for much larger fluid reservoirs 350 because the reservoir need not reside within the pump 110. The reservoir 350 may be placed in or on the body and may be refillable.

The pump 110 may be a bidirectional pump, meaning that it capable of pumping fluid 115 in both directions through the cannula 105. As used herein, the pump motor 315 may receive a positive signal causing the pump 110 to operate in a first direction. Operating in the first direction is understood to mean that fluid 115 is transferred from the reservoir 350 through the cannula 105 and into the anterior chamber 190 of the eye 140. Conversely, the pump motor 315 may receive a negative signal causing the pump 110 to operate in a second direction. Operating in the second direction is understood to mean that fluid 115 is transferred from the anterior chamber 190 of the eye 140 through the cannula 105 and into the reservoir 350.

The present invention is also a broadly innovative concept for neuroscience research. The main alternatives for sustained delivery of small volumes to the eye or other organ would be an osmotic pump (e.g., Alzet®, Durect Corp, Cupertino, Calif.), peristaltic pump (e.g., SynchroMed®, Medtronic Corp, Minneapolis, Minn.), or syringe pump (e.g., Legato®, KD Scientific Inc., Holliston, Mass.). Osmotic pumps are easiest to implant, but they rely on osmosis of water to extrude their contents (usually a medicant).

Peristaltic pumps can be electronically programmed to deliver fluid at different rates, but the implantable ones only infuse fluid and are too large for most research animals.

Syringe pumps can both withdraw and inject pico liters of fluid at programmable rates, but commercially available ones all achieve such volumes via small syringes while the pump itself sits bench side. Moreover, none of these alternatives have a built-in feedback mechanism that regulates flow.

In lieu of an implantable system 100, a programmable syringe pump 110 with analog input control (e.g., Ultra 4400, Harvard Apparatus, Holliston, Mass. or SYR-1200, J-KEM Scientific Inc., St. Louis, Mo.) may be used in conjunction with a pressure sensor 120. The pump 110 may be controlled by a computer program (e.g., Labview®, National Instruments, Austin, Tex.) via a multi-function data acquisition card (e.g., NI PCIe-7851R, National Instruments). A long cannula 105 may connect the eye 140 to the pump 110 and pressure sensor 120 via a tether system that mitigates twisting and pulling.

The pump 110 has finite capacity, which is purposefully small in order to make it implantable. Fortunately, the fluid 115 movement associated with a given pressure change in the rat eye 140 is even smaller. However, if there is net flux for a period of time, the piston 325 may reach its upper/lower capacity limit, and the pump head 310 may need emptying/filling. The pump head 310 may be enlarged to overcome the need for emptying/filling, or the mini-syringe pump design may be replaced with one based on a peristaltic pump which would allow for a bigger reservoir, such as a fluid-filled sac strapped to the animal's back.

Controller Circuit

Figure 5:
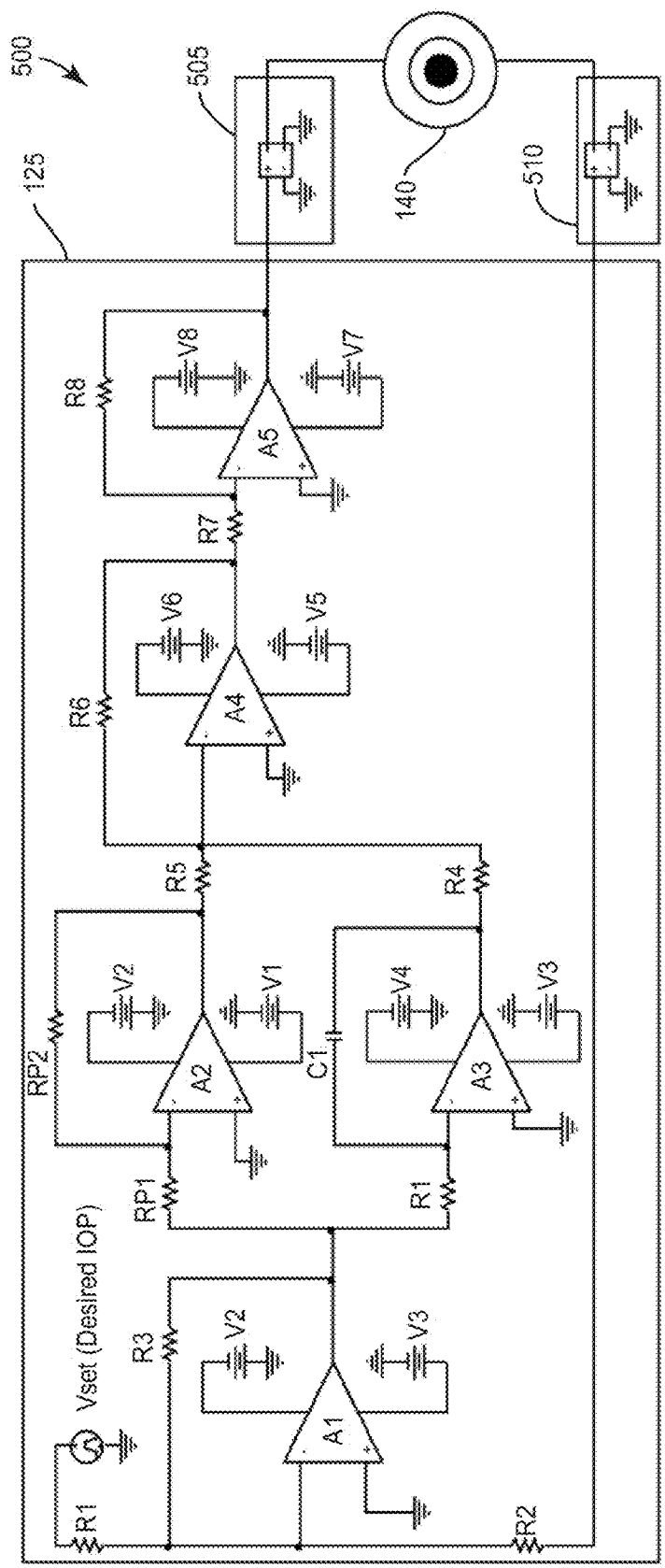
FIG. 5 is a schematic of a controller circuit.

The controller 125 may comprise a controller circuit 500 as illustrated schematically in FIG. 5. The controller circuit 500 may be designed with PI (proportional-integral) feedback loops, and may comprise comparator (A1), proportional (A2), integral (A3), summing (A4), and inverting (A5) amplifiers. Pump block 505 and sensor block 510 may linearly convert voltage to pressure and vice versa. The proportional element (A1) scales controller output in proportion to the instantaneous error between desired and measured IOP signals. The integral element (A2) further adjusts controller 125 output based on the time integral of the error, speeding arrival at the desired IOP at the possible cost of transiently overshooting it. More complex circuits are possible to fine tune the response dynamics of the controller 125 but they are not likely needed for IOP control because the controller 125 response time is virtually instantaneous with respect to normal IOP changes.

FIGS. 6A through 6C illustrate simulations of the controller circuit 500 response to a step change in desired IOP level from 20 to 40 mmHg. In FIG. 6A, the desired IOP set point is increased at time equal to 1 ms. The voltage sent to the pump drive motor 315 as shown in FIG. 6B rapidly increases due to the disparity between desired and actual IOP, then gradually decreases as the controller circuit 500 senses the increasing IOP. In FIG. 6C, the positive drive of the pump 110 by the controller circuit 500 causes the measured IOP to increase up to the desired set point of 40 mmHg, with a small delay as the controller circuit gradually turns off the pump 110.

The result of the operation of the controller circuit 500 is that IOP is driven with a slight delay to the specified level and held there. Relative to natural IOP fluctuations this delay is negligible. The controller 125 set point can be high to raise IOP above the normal level in order to study the cause and effect of the glaucoma in animal models or the set point can be set normal to lower IOP and possibly arrest glaucoma in human patients with high IOP. The controller can also be configured with other temporal waveforms besides a constant, meaning the eye 140 can be exposed to any IOP history that one desires.

No explicit formula exists for specifying resistor and capacitor values for the controller circuit of FIG. 5 that give stable controller 125 behavior. The circuit 500 may be tuned in connection with the pressure sensor 120 and pump 110 to some extent by trial and error. This tuning may be simplified by the marked difference in IOP and controller 125 dynamics. For example, differential elements often used for overshoot management may not be necessary for this application since the overshoot duration is extremely brief on physiological scales. Issues of oscillation that can make circuit tuning difficult are thus avoided.

Long-term powering of the circuit 500 in an animal and mechanical wear down of pump elements from over usage may be addressed in various embodiments of the smart pump 110 by, for example, adding switches that would allow the motor 315 to run only for short periods of time at the longest intervals that maintain IOP at the desired level or by incorporating a RF-to-DC converter in the circuit 500 that harvests continuous energy from an external RF source.

While the smart pump system 100 can be applied to any mammalian eye or relevant disease model, the inventors used the rat glaucoma model for instrument development and testing since the rat glaucoma model is well established and documented, and the animal size presents design challenges relevant to prospective applications of the system 100 to larger mammals and humans. However, various embodiments may be used to deliver a medicant or other treatment via the smart pump 110 in response to any measurable parameter and, thus, the system 100 is not limited to applications involving the eye 140.

Instrument Calibration and Testing

Before testing tetherable and implantable systems 100 on living animals, they are calibrated to read IOP signals correctly and hold the signals at desired levels stably in anesthetized animals. Adult Brown-Norway rats (0.3-0.5 kg) are anesthetized with a mixture of ketamine (75 mg/kg) and xylazine (7.5 mg/kg) and mounted on a heating pad in a stereotaxic. The ocular cannula 105 is inserted into the anterior chamber 190 and secured to the eye 140. A 33G needle is then inserted into the same eye 140 and held in place with a manipulator. Coupled to the needle via a T-valve and tubing is a mercury manometer in parallel with a reservoir of physiological saline [49]. First, the controller 125 set point is calibrated by raising the reservoir to different heights above eye level and recording the voltage output of the pressure sensor 120 for corresponding manometer IOP levels. The lab tonometer is concurrently calibrated for noninvasive IOP measurements in experiments below. Once a look-up table relating sensor 120 output to circuit voltage is complete, the manometer line is disconnected and fed to a calibrated pressure transducer (Model 1050, Stoelting Comp, Wood Dale, Ill.). The IOP signals from this and the smart pump system 100 are then digitized to a computer while performing three tests: 1) varying reservoir height, 2) varying controller 125 set point, and 3) apply varying physical force to the cornea 155 with a blunt probe mounted on a micromanipulator. A smart pump 110 design is deemed ready for living animal testing when it can raise or lower IOP to a controller-specified level and hold it steady for different static and dynamic conditions with minimal oversight and upkeep.

Tethered System

Figure 7C:
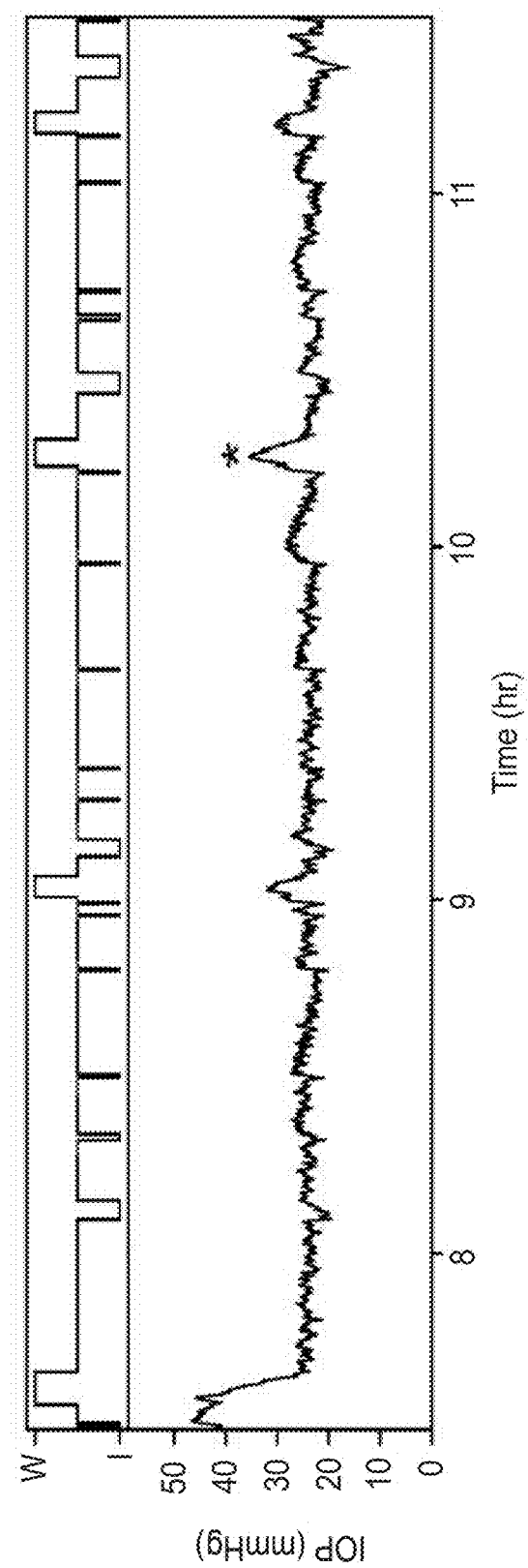

A prototype system 100 was developed comprising non-miniaturized embodiments of the pump 110, pressure sensor 120, and controller 125. The prototype system 100 was too large to be implanted into the animal and was tethered to the animal by the cannula 105. After implanting the cannula 105 into the anterior chamber 190 of one eye 140 of a rat. The IOP of the implanted eye 140 was recorded over a period of 28 hours. FIG. 7A shows the measured IOP during the 28 hour period while the system 100 was running in open-loop control (pressure measurement only; pump 110 was not operational). A circadian rhythm of about 5-7 mmHg in amplitude can be seen in FIG. 7A, with pressure highest during the animal's subjective night. The system 100 was operated in closed-loop control (pump 110 operational) as shown in FIG. 7B. The system 100 ran in open-loop control until the first arrowhead. At each successive arrowhead, the controller 125 set point was switched to 35, 45, 25, and back to 35 mmHg. FIG. 7C illustrates an expanded view of the IOP record in FIG. 7C from 7.5 to 11.5 hours and the corresponding pump 110 action (above graph). The system 100 was configured to adjust IOP within ±3 mmHg of the set point. Set point changes, intrinsic fluctuations, or external perturbations (indicated by the asterisk) caused the pump 110 to withdraw (W) or inject (I) as needed to maintain IOP within the prescribed range.

Figure 8A:
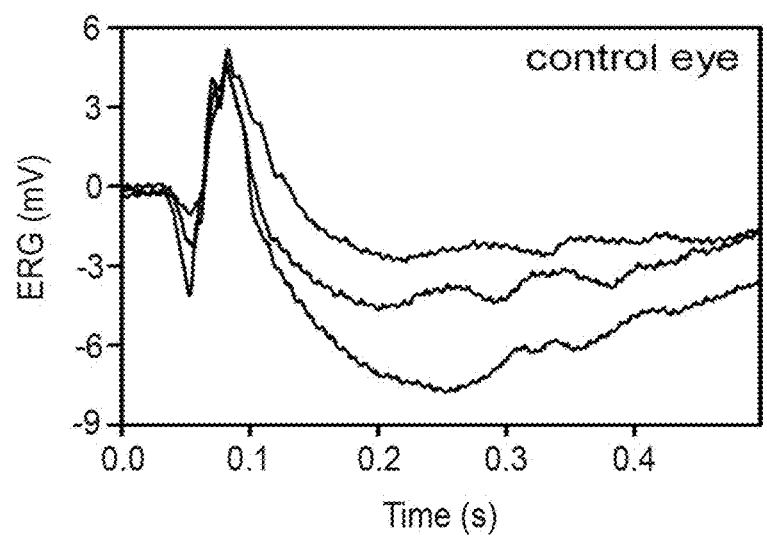
FIGS. 8A and 8B are graphs of ERG responses of a control eye and an implanted eye, respectively, to three brief light flashes of increasing intensity.
Figure 8B:
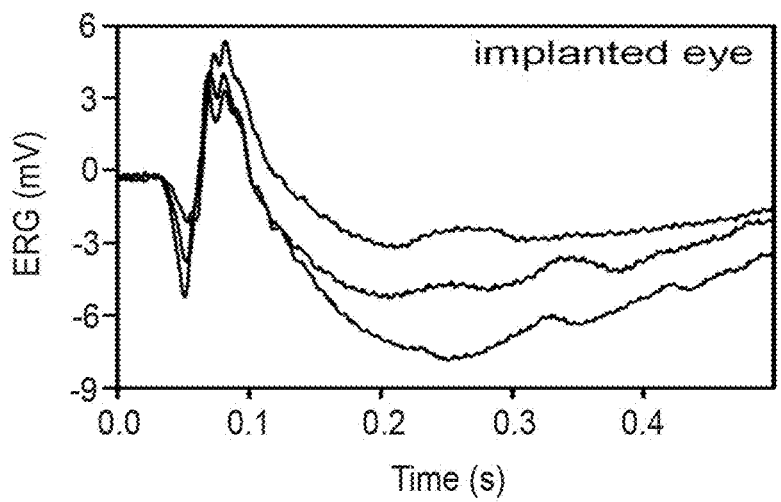

In order to demonstrate that the retina 185 of the implanted eye 140 was functionally healthy as well as structurally normal, electroretinogram (ERG) recordings from the control (non-implanted) eye 140 (FIG. 8A) and the implanted eye 140 (FIG. 8B) were taken 6 weeks after implantation. The recordings were made by anesthetizing the rat with isoflurane and resting contact lenses rimmed by gold wire electrodes on the corneas 155. Reference and ground needle electrodes were inserted in the scalp and tail. Full-field flashes were delivered repetitively to both eyes 140 simultaneously in a dark room and evoked responses were averaged for different flash intensities (4.3, 8.6, and 17.2 kcd/m$^2$). The flashes had a duration of 10 ms and were spaced 3 seconds apart. The flashes evoked a large a-wave (first negative peak in FIGS. 8A and 8B) and b-wave (first positive peak in FIGS. 8A and 8B). The ERGs from both eyes 140 virtually overlay in waveform, amplitude, and sensitivity. The robust a- and b-waves confirm that outer retinal neurons of the implanted eye 140 were physiologically normal. Oscillatory potentials suggest that the inner retinal function was also normal.

Wireless Implantable System

Various embodiments may comprise a wireless implantable IOP control system 100 wherein the controller 125 comprises a wireless transmitter circuit 132. The wireless system 100 may comprise a miniaturized and self-powered pump 110, pressure sensor 120, and cannula 105 coupled to the exterior body of implanted within the body. The pump 110 may maintain wireless communication with the controller 125. In various embodiments, the controller 125 may also be implanted within the body.

Methods of IOP Control

Figure 9:
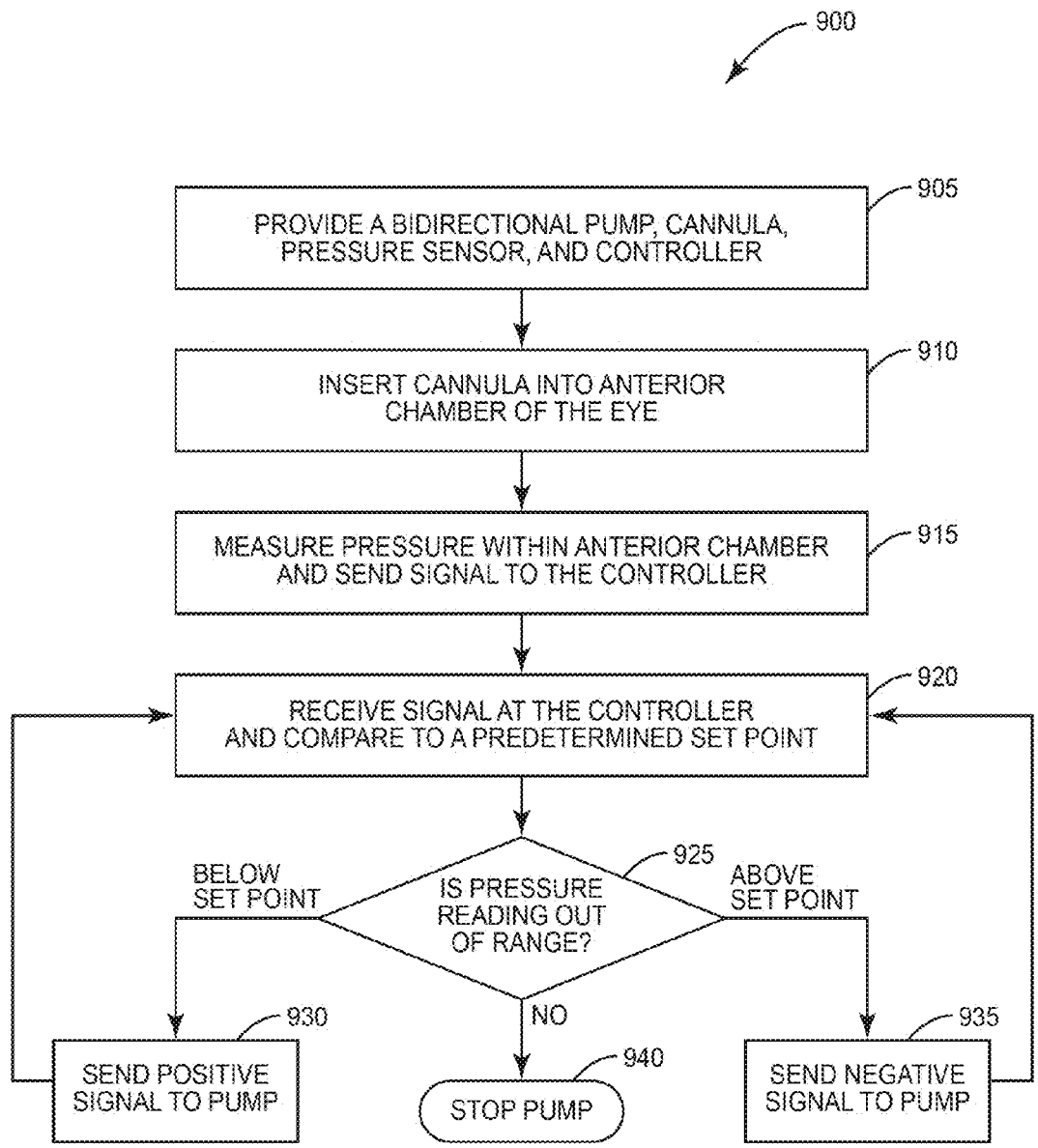
FIG. 9 is a flow diagram of an exemplary method for regulating pressure within a portion of a human or animal body.

FIG. 9 illustrates an exemplary method 900 for adjusting IOP according to various embodiments. At step 905, a bidirectional fluid pump 110, a cannula 105, a pressure sensor 120, and a controller 125 are provided. The pump 110 comprises a reservoir containing a volume of fluid 115. The cannula 105 is coupled to the reservoir so that the pump 110 can move the fluid 115 in either direction through the cannula 105. The cannula is inserted into the anterior chamber 190 of the eye 140 at step 910. The pressure sensor 120 measures the pressure within the anterior chamber 190 and sends a signal to the controller 125 (step 915). The controller at step 920 receives the signal from the pressure sensor 120 and compares the signal to a predetermined range about a set point. At step 925, if the pressure reading in less than the set point, the controller 125 sends a positive signal to the pump 110 (step 930) such that the pump 110 operates in a first direction and injects fluid 115 through the cannula 105 into the anterior chamber 190 of the eye 140. If the pressure reading is greater than the set point, the controller 125 sends a negative signal to the pump 110 (step 935) such that the pump 110 operates in a second direction and withdraws fluid 115 from the anterior chamber 190 of the eye 140 through the cannula 105 and into the pump reservoir. The controller 125 continues to monitor the pressure measurement (step 920) and determines whether the reading is within range (step 925). When the controller 125 determines that the pressure measurement is within the predetermined range, the pump 110 is turned off at step 940.

Applications

Glaucoma Induction

This invention represents a new and powerful tool for glaucoma research that will help to speed progress in the fight against this debilitating disease. Researchers learn about the mechanisms by which the disease inflicts damage upon the eye 140 by using animal models in which IOP is increased by natural or experimental means. Current methods of inducing glaucoma in animals may work, but they have significant limitations. Too much effort is spent treating animals that fail to develop glaucoma, measuring IOP by hand on a semi-daily basis (which is too sparse to catch momentary spikes in pressure), and averaging datasets to overcome variability across animals in the amount and time course of IOP changes. The present invention eliminates these issues with its groundbreaking promise of near-zero failure rate, near-effortless pressure monitoring, and near-constant pressure changes that can be fully specified. The present invention thereby stands to shift the paradigm that glaucoma researches use to learn about the causes and effects of the disease.

Glaucoma Treatment

When a clinical diagnosis of glaucoma is made, the standard treatment is to administer drugs that reduce aqueous fluid production by the ciliary body of the eye 140. Drug treatment can lower IOP and arrest the progression of the disease if the patient faithfully applies the medicine, but it is not a preemptive solution because the drugs are expensive and can have undesirable side effects. In cases where glaucoma medications do not lower IOP enough, laser trabeculoplasty may be performed or aqueous drainage tubes may be inserted to help relieve pressure. These solutions have greater certainty with the heightened risk of surgical complications, lowering IOP too much, or retreatment to reopen the drainage field.

The present invention may be valuable for glaucoma treatment, especially in patients for whom drugs, surgery, and drainage tubes are not viable options. Benefits of the present invention over glaucoma medication are that there would be no negative side effects of the drugs, no missed dosages, and less overall costs since medicines are expensive and taken for the patient's life. Benefits over eye surgery or drainage implants are that there would be no abnormal or prolonged spikes or drops in pressure that often follow these procedures which can cause additional damage.

The system 100 could be mounted on the inner wall of the supraorbital ridge and draw fluid via a fine cannula 105 implanted in the eye 140 as needed to lower and hold pressure at a normal level, perhaps dumping the excess fluid in the conjunctival sac. The present invention would, for the first time, give clinicians complete control of eye pressure as well as round-the-clock feedback on pressure for managing that control thus preventing abnormal IOP swings from spontaneously occurring or surgically-induced events that may damage optic nerve cells. Moreover, since the pressure sensor signal can be transmitted to an external receiver, the invention would allow clinicians to continually monitor the patient's IOP and the performance of the system from their offices.

Programmable and Implantable Pump for Delivery of Small Fluid Volumes

Abnormal pressure is not just a symptom of glaucoma. For example, Meniere's disease is associated with distension of fluid compartments and compression of the neurosensory organ in the cochlea due to high endolymphatic pressure [51-53]. Much like the state-of-affairs for glaucoma, current animal models of the disease use surgical, mechanical, or pharmacological methods to induce cochlear hypertension with inconsistent, unpredictable, and/or irreversible consequences. The smart pump system 100 can thus provide a paradigm-shifting tool for systematically and controllably studying the etiology of that disease as well. Other possible areas of application are intracranial pressure disorders (head trauma, hydrocephalus, migraines, etc.).

The invention has niche applications beyond glaucoma as a programmable and implantable pump for delivery of small fluid volumes. The main commercially-available alternatives would be osmotic pumps (Alzet®, Durect Corp, Cupertino, Calif.), generic syringe pumps (e.g., Legato®, KD Scientific Inc., Holliston, Mass.), and peristaltic insulin pumps (SynchroMed®, Medtronic Corp, Minneapolis, Minn.). Osmotic pumps are easiest to implant but they rely on the osmosis of water to extrude their contents (usually a drug), which is a fixed steadily-decaying process.

Syringe pumps can withdraw and inject pico liters fluid at fully programmable rates, but they all achieve such small volumes via small syringes. The pump itself is not implantable or wearable.

Insulin pumps are programmable battery-powered devices, some of which are implantable. They infuse fluid only and are several fold larger than the pump described here. They do not have a sensor or controller either to provide a feedback mechanism that regulates flow.

REFERENCES

1. Quigley H A (1999) Neuronal death in glaucoma. *Prog Retin Eye Res* 18:39-57. PMID: 9920498
2. Morrison J C, Johnson E C, Cepurna W, Jia L (2005) Understanding mechanisms of pressure-induced optic nerve damage. *Prog Retin Eye Res* 24:217-40. PMID: 15610974
3. Shiose Y, Kitazawa Y, Tsukahara S, Akamatsu T, Mizokami K, Futa R, Katsushima H, Kosaki H (1991) Epidemiology of glaucoma in Japan—a nationwide glaucoma survey. *Jpn J Ophthalmol* 35:133-55. PMID: 1779484
4. Klein B E, Klein R, Sponsel W E, Franke T, Cantor L B, Martone J, Menage M J (1992) Prevalence of glaucoma. The Beaver Dam Eye Study. *Ophthalmology* 99:1499-1504. PMID: 1454314
5. John, S W (2005) Mechanistic insights into glaucoma provided by experimental genetics. The Cogan Lecture. *Invest Ophthalmol Vis Sci* 39:951-62. PMID: 16043833
6. McKinnon S J, Schlamp C L, Nickells R W (2009) Mouse models of retinal ganglion cell death and glaucoma. *Exp Eye Res* 88:816-24. PMID: 19105954
7. Almasieh M, Wilson A M, Morquette B, Vargas J L C, Di Polo A (2012) The molecular basis of retinal ganglion cell death in glaucoma. *Prog Retin Eye Res* 31:152-81. PMID: 22155051
8. Gaasterland D, Kupfer C (1974) Experimental glaucoma in rhesus monkey. *Invest Ophthalmol Vis Sci* 13:455-57. PMID: 4208801
9. Quigley H A, Hohman R M (1983) Laser energy levels for trabecular meshwork damage in the primate eye. *Invest Ophthalmol Vis Sci* 24:1305-7. PMID: 6885314
10. Ueda J, Sawaguchi S, Hanyu T, Yaoeda K, Fukuchi T, et al. (1998) Experimental glaucoma model in the rat induced by laser trabecular photocoagulation after an intracameral injection of India ink. *Jpn J Ophthalmol* 42:337-44. PMID: 9822959
11. Aihara M, Lindsey J, Weinreb R N (2003) Experimental mouse ocular hypertension: establishment of the model. *Invest Ophthalmol Vis Sci* 44:4314-20. PMID: 14507875
12. Moore C, Milne S, Morrison J (1993) A rat model of pressure-induced optic nerve damage. *Invest Ophthalmol Vis Sci* 34:1141.
13. Garcia-Valenzuela E, Shareef S, Walsh J, Sharma S C (1995) Programmed cell death of retinal ganglion cells during experimental glaucoma. *Exp Eye Res* 61:33-44. PMID: 7556468
14. Grozdanic S D, Betts D M, Sakaguchi D S, Kwon Y H, Kardon R H, Sonea I M (2003) Temporary elevation of the intraocular pressure by cauterization of vortex and episcleral veins in rats causes functional deficits in the retina and optic nerve. *Exp Eye Res* 77:27-33. PMID: 12823985
15. Morrison J C, Moore C G, Deppmeier L M, Gold B G, Meshul C K, Johnson E C (1997) A rat model of chronic pressure-induced optic nerve damage. *Exp Eye Res* 64:85-96. PMID: 9093024
16. Gross R L, Ji J, Chang P, Pennesi M, Yang Z, Zhang J, Wu S M (2003) A mouse model of elevated intraocular pressure: retina and optic nerve findings. *Trans Am Ophthalmol Soc* 101:163-9. PMID: 14971574
17. Ruiz-Ederra J, Garcia M, Hernandez M, Urcola H, Hernández-Barbáchano E, Araiz J, Vecino E (2005) The pig eye as a novel model of glaucoma. *Exp Eye Res* 81:561-9. PMID: 15949799
18. Ruiz-Ederra J, Verkman A S (2006) Mouse model of sustained elevation in intraocular pressure produced by episcleral vein occlusion. *Exp Eye Res* 82:879-84. PMID: 16310189
19. Fu C T, Sretavan D (2010) Laser-induced ocular hypertension in albino CD-1 mice. *Invest Ophthalmol Vis Sci* 51:980-90. PMID: 19815738
20. Sappington R M, Carlson B J, Crish S D, Calkins D J (2010) The microbead occlusion model: a paradigm for induced ocular hypertension in rats and mice. *Invest Ophthalmol Vis Sci* 51:207-16. PMID: 19850836
21. Morrison J C, Cepurna W O, Guo Y, Johnson E C (2011) Pathophysiology of human glaucomatous optic nerv damage: insights from rodent models of glaucoma. *Exp Eye Res* 93:156-64. PMID: 20708000
22. Katz M L, Robison W G Jr (1986) Evidence of cell loss from the rat retina during senescence. *Exp Eye Res* 42:293-304. PMID: 3709700
23. Cavallotti C, Artico M, Pescosolido N, Feher J (2001) Age-related changes in rat retina. *Jpn J Ophthalmol* 45:68-75. PMID: 11163048
24. Cepurna W O, Kayton R J, Johnson E C, Morrison J C (2005) Age related optic nerve axonal loss in adult Brown Norway rats. *Exp Eye Res* 80:877-84. PMID: 15939045
25. Passaglia C L, Troy J B, Rüttiger L, Lee B B (2002) Orientation sensitivity of ganglion cells in primate retina. *Vision Res* 42:683-694. PMID: 11888534
26. Freeman D F, Heine W F, Passaglia C L (2010) Single-unit in vivo recordings from the optic chiasm of rat. *J Vis Exp* 38, pii: 1887, doi:10.3791/1887. PMID: 20364119
27. Heine W F, Passaglia C L (2011) Spatial receptive field properties of rat retinal ganglion cells. *Vis Neurosci* 28:403-17. PMID: 21944166
28. Schnell C R, Debon C, Percicot C L (1996) Measurement of intraocular pressure by telemetry in conscious unrestrained rabbits. *Invest Ophthalmol Vis Sci* 37:958-965. PMID: 8631639
29. McLaren J W, Brubaker R F, FitzSimmons J S (1996) Continuous measurement of intraocular pressure in rabbits by telemetry. *Invest Ophthalmol Vis Sci* 37:966-75. PMID: 8631640
30. Walter P (1999) Development of a completely encapsulated intraocular pressure sensor. *Ophthalmic Res* 32:278-84. PMID: 11015039
31. Li Y, Liu J H (2008) Telemetric monitoring of 24 h intraocular pressure in conscious freely moving C57BL/6J and CBA/Caj mice. *Mol Vis* 14:745-9. PMID: 18431454
32. Xue N, Chang S P, Lee J B (2011) A SU-8-based compact implantable wireless pressure sensor for intraocular pressure sensing application. *Conf Proc IEEE Eng Med Biol Soc* 2011:2854-7. PMID: 22254936
33. Todani A, Behlau I, Fava M A, Cade F, Cherfan D G, Zakka F R, Jakobiec F A, Gao Y, Dohlman C H, Melki S A (2011) Intraocular pressure measurement by radio wave telemetry. *Invest Ophthalmol Vis Sci* 52:9573-9580. PMID: 22039243
34. Ha D, de Vries W N, John S W, Irazoqui P P, Chappell W J (2012) Polymer-based miniature flexible capacitive pressure sensor for intraocular pressure (IOP) monitoring inside a mouse eye. *Biomed Microdevices* 14:207-15. PMID: 21096710
35. Leonardi M, Leunberger P, Bertrand D, Bertsch A, Renaud P (2004) First steps toward non-invasive intraocular pressure monitoring with a sensing contact lens. *Invest Ophthalmol Vis Sci* 45:3113-17. PMID: 15326128
36. Sánchez I, Laukhin V, Moya A, Martin R, Ussa F, Laukhina E, Guimera A, Villa R, Rovira C, Aguilo J, Veciana J, Pastor J C (2011) Prototype of a nanostructured sensing contact lens for noninvasive intraocular pressure monitoring. *Invest Ophthalmol Vis Sci* 52:8310-5. PMID: 21948548
37. El-Khatib F H, Jiang J, Damiano E R (2007) Adaptive closed-loop control provides blood-glucose regulation using dual subcutaneous insulin and glucagon infusion in diabetic Swine. *J Diabetes Sci Technol* 1:181-92. PMID: 19888405
38. Bruttomesso D, Farret A, Costa S, Marescotti M C, Vettore M, Avogaro A, Tiengo A, Dalla Man C, Place J, Facchinetti A, Guerra S, Magni L, De Nicolao G, Cobelli C, Renard E, Maran A (2009) Closed-loop artificial pancreas using subcutaneous glucose sensing and insulin delivery and a model predictive control algorithm: preliminary studies in Padova and Montpellier. *J Diabetes Sci Technol* 3:1014-21. PMID: 20144414
39. Jacobs P G, El Youssef J, Castle J R, Engle J M, Branigan D L, Johnson P, Massoud R, Kamath A, Ward W K (2011) Development of a fully automated closed loop artificial pancreas control system with dual pump delivery of insulin and glucagon. *Conf Proc IEEE Eng Med Biol Soc* 2011: 397-400. PMID: 22254332
40. Freeman D K, Heine W F, Passaglia C L (2008) The maintained discharge of rat retinal ganglion cells. *Vis Neurosci* 18:1-10. PMID: 18634718. PMID: 18634718
41. Heine W F, Passaglia C L (2011) Spatial receptive field properties of rat retinal ganglion cells. *Vis Neurosci* 28:403-17. PMID: 21944166
42. Sun S Y, Wang W, Zucker I H, Schultz, H D (1999) Enhanced peripheral chemoreflex function in conscious rabbits with pacing-induced heart failure. *J Appl Physiol* 1264-72. PMID: 10194212
43. McNulty R, Wang H, Mathias R T, Ortwerth B J, Truscott R J W, Bassnett S (2004) Regulation of tissue oxygen levels in the mammalian lens. *J Physiol* 559:883-98. PMID: 15272034
44. Molteno A C (1969) New implant for drainage in glaucoma: clinical trial. *Brit J Ophthalmol* 53:161-8. PMID: 4900144
45. Ball S F, Ellis G S, Herrington R G, Liang K (1992) Brown's superior oblique tendon syndrome after Baerveldt glaucoma implant. *Arch Ophthalmol* 110:1368. PMID: 1417532
46. Raviv T, Greenfield D S, Liebmann J M, Sidoti P A, Ishikawa H, Ritch R (1998) Pericardial patch grafts in glaucoma implant surgery. *J Glaucoma* 7:27-32. PMID: 9493112
47. Hughes A (1979) A schematic eye for the rat. *Vision Res* 19:569-88. PMID: 483586
48. Akula J D, Favazza T L, Mocko J A, Benador I Y, Asturias A L, Kleinman M S, Hansen R M, Fulton A B (2010) The anatomy of the rat eye with oxygen-induced retinopathy. *Doc Ophthalmol* 120:41-50. PMID: 19820974
49. Passaglia C L, Guo X, Chen J, Troy J B (2004) Tono-Pen XL calibration curves for cat, cow, and sheep. *Vet Ophthalmol* 7:261-4. PMID: 15200622
50. Selles-Navarro I, Villegas-Perez M P, Salvador-Silva M, Ruiz-Gomez J M, Vidal-Sanz M (1996) Retinal ganglion cell death after different transient periods of pressure-induced ischemia and survival intervals: a quantitative in vivo study. *Invest Ophthalmol Vis Sci* 37:2002-14. PMID: 8814140
51. Mateijsen D J, Rosingh H J, Wit H P, Albers F W. (2001) Perilymphatic pressure measurement in patients with Meniere's disease. *Eur Arch Otorhinolaryngol* 258:1-4. PMID: 112771426
52. Takumida M, Akagi N, Anniko M (2008) A new animal model for Meniere's disease. Acta Otolaryngologica 128: 263-71. PMID: 17851960
53. Salt A N, Plontke A K (2010) Endolymphatic hydrops pathophysiology and experimental models. *Otolaryngol Clin North Am* 43:971-83. PMID: 20713237
54. Wells J K, Crampton W G R (2006) A portable bio-amplifier for electric fish research: design and construction. *Neotrop Ichthyol* 4:295-9

GLOSSARY OF CLAIM TERMS

Anterior chamber: The space defined by the cornea on one side and the iris and pupil on the other side within a mammalian eye.

Bidirectional pump: A pump that can be selectively driven in "forward" and "reverse" directions such that a fluid moved by the pump can be injected into or withdrawn from a contained area.

Cannula: Very thin and generally flexible tubing able to conduct a liquid.

Intraocular eye pressure: The pressure exerted by fluid within an eye.

Piezoelectric resistor: A device in which the electrical resistivity changes when the device is subjected to mechanical stress.

Set point: A setting inputted to a controller that represents a desired value for a parameter. The set point may be a numeric value or a representation of a numeric value such as a proportional voltage.

Signal: A transmission generated by a sensor and directed to a controller. The transmission may be a voltage current, radio waves, infrared light, or any other technique for conveying a signal known in the art now or in the future.

Wheatstone bridge: An electrical circuit comprising four resistors arranged in a four-arm bridge circuit used to measure a change in resistance.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between.

What is claimed is:

1. A method for regulating intraocular eye pressure, comprising:
- providing a bidirectional pump comprising a motor, a piston coupled to the motor, and a reservoir containing a fluid;
- providing a pressure sensor operative to sense intraocular eye fluid pressure;
- providing a cannula comprising a first end coupled to the reservoir such that movement of the piston causes the fluid to flow through the cannula, and a second end configured for insertion into the eye such that fluid is either withdrawn or injected into the eye depending on an operating direction of the pump;
- providing a controller operatively coupled to the pump and pressure sensor;
- implanting the pump, pressure sensor, and cannula into the eye;
- inserting at least a portion of the cannula into an anterior chamber of the eye;
- sensing fluid pressure within the anterior chamber and sending a signal to the controller;
- receiving the signal at the controller and comparing the signal to a set point; and
- causing the pump to operate in a first direction when the signal is below the set point and causing the pump to operate in a second direction when the signal is above the set point.

2. The method of claim 1, wherein the piston is in communication with a fluid contained in the reservoir.

3. The method of claim 1, further comprising coupling the pressure sensor to the piston.

4. The method of claim 1, wherein causing the pump to operate in the first direction injects fluid into the eye.

5. The method of claim 1, wherein causing the pump to operate in the second direction withdraws fluid from the eye.

* * * * *